(12) United States Patent
Catlin

(10) Patent No.: US 9,986,978 B2
(45) Date of Patent: Jun. 5, 2018

(54) SIMPLE SAMPLE STOOL COLLECTION, CONTAINMENT, AND SPECIMEN DISBURSEMENT SYSTEM

(71) Applicant: Catlin Enterprises. Inc., Austin, TX (US)

(72) Inventor: George Catlin, Austin, TX (US)

( * ) Notice: Subject to any disclaimer, the term of this patent is extended or adjusted under 35 U.S.C. 154(b) by 290 days.

(21) Appl. No.: 14/874,423

(22) Filed: Oct. 3, 2015

(65) Prior Publication Data

US 2017/0095232 A1    Apr. 6, 2017

(51) Int. Cl.
| A47K 13/16 | (2006.01) |
| A47K 11/02 | (2006.01) |
| A61B 10/00 | (2006.01) |

(52) U.S. Cl.
CPC .......... *A61B 10/0038* (2013.01); *A47K 11/02* (2013.01); *A47K 13/16* (2013.01)

(58) Field of Classification Search
CPC . A61B 10/0038; A47K 13/08; B65D 53/1691
See application file for complete search history.

(56) References Cited

U.S. PATENT DOCUMENTS

| 3,540,433 | A | * | 11/1970 | Brockman | A61B 10/0038 4/144.1 |
| 5,463,782 | A | | 11/1995 | Carlson et al. | |
| 6,415,455 | B1 | | 7/2002 | Slaon, III et al. | |
| 6,434,762 | B2 | | 8/2002 | Gordon | |
| 6,640,355 | B1 | | 11/2003 | Samide | |
| 6,653,149 | B1 | | 11/2003 | Tung et al. | |
| 2001/0042264 | A1 | * | 11/2001 | Sloan, III | A47K 11/105 4/315 |
| 2003/0021735 | A1 | | 1/2003 | House | |
| 2004/0013322 | A1 | * | 1/2004 | Taylor | B65D 33/20 383/62 |
| 2005/0027266 | A1 | * | 2/2005 | Howlett | A61G 9/00 604/317 |
| 2007/0245486 | A1 | * | 10/2007 | Battle | A61B 10/0038 4/661 |

* cited by examiner

*Primary Examiner* — Michael C Stout
(74) *Attorney, Agent, or Firm* — Michael A. Ervin; M.A. Ervin & Associates

(57) ABSTRACT

A stool collection, containment, and specimen disbursement system for facilitating easier stool collection while protecting the samples from bio-contamination and providing easier functionality for patients, diagnostic centers, and labs.

9 Claims, 3 Drawing Sheets

SIMPLE SAMPLE STOOL COLLECTION, CONTAINMENT, AND SPECIMEN DISBURSEMENT SYSTEM

BACKGROUND

Stool collection ordered by physicians for the purposes of a variety of lab tests and assays can be a tedious, messy and possibly lead to bio-contamination of the sample. The sample collection typically requires the patient to defecate into a large plastic collection bowl that sits on top of the toilet bowl. After the primary sample is deposited into the collection bowl, the patient is required to wear plastic gloves and use a tongue depressor to collect measured samples from the collection bowl and distribute these samples into a variety (5-10) of containers and assay tubes dedicated for each test. After distributing the measure samples into the various collection jars and tubes, the patient is then required to refrigerate and/or freeze the samples to limit containment of the samples. This is laborious, distasteful process that often goes uncompleted due to the nature of the collection. Patient compliance suffers as a result and many tests may not be performed as a result. This collection process is typically done at home which further increases patient non-compliance.

Accordingly a need exists to change this dynamic. There is a need for a collection methodology that facilitates easier collection, protect sample from bio-contamination and provide easier functionality for patients, diagnostic centers and labs.

SUMMARY

This need is met by a novel device concept for collection of stool samples for diagnostic testing. It is designed to facilitate easier collection, containment, protection of sample from bio-contamination and to provide easier functionality for patients, diagnostic centers and labs. It includes a variety of features that enable distributing, re-sealing and extracting specific sample quantities.

The need can be met by a stool collection, containment, and specimen disbursement system including at least: a polymeric toilet seat cover that can fit over a variety of toilet seats; an elastic band that secures the toilet seat cover to the toilet seat; a polymeric funnel that extends from the toilet seat cover into the toilet bowl and is connected to the inside of a polymeric collection bag by means of perforated tear lines on either side of the collection bag; an opening in the polymeric funnel large enough to allow urine to bypass the collection bag and flow directly into the toilet bowl; a looped handle connected to the perforated tear lines and used to tear the funnel away from the collection bag; a primary seal with adhesive at the opening of the containment bag with an attached primary pull seal tab that allows the removal of an adhesive cover sheet; a larger secondary seal with adhesive positioned outside of the funnel along the outside of the collection bag with a removable adhesive cover sheet; and a variable flow rate nozzle on one side of the collection bag.

DETAILED DESCRIPTION

Figure 1:
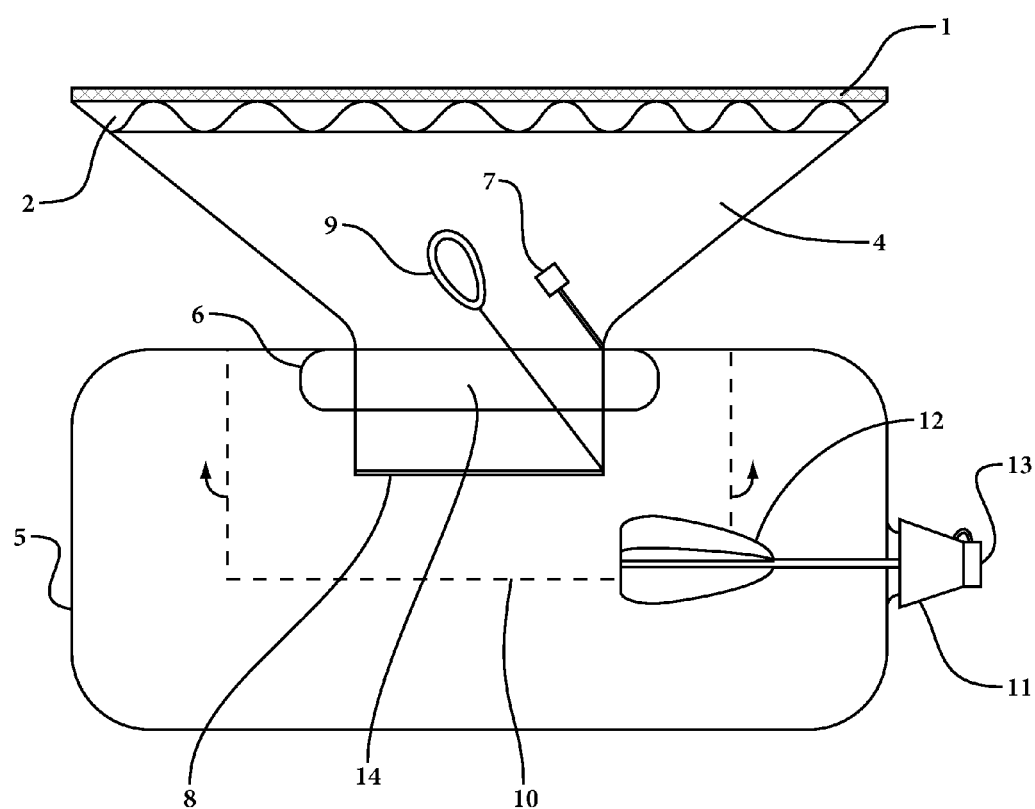
FIG. 1 is a side perspective view of an embodiment of the proposed device.

Referring to FIG. 1 the proposed solution includes a thin polymeric toilet seat cover 2 to fit a variety of toilet seats. The toilet seat cover 2 is secured by an elastic band 1. The band can be produced from any number of elastomeric polymer or rubber materials. A polymeric funnel 4 extends from the toilet seat cover and connects to the inside of a polymeric collection bag 5. The seat cover extends into the toilet bowl and transitions into the funnel. The seat cover is sufficiently wide and long to cover the toilet seat. It may be made of a light plastic material that is lightweight, biodegradable and strong enough to accommodate the physical demands of the funnel, which can be made of the same material (i.e the funnel being an extension of the toilet seat). The seat cover/funnel may be made of a material that is flushable.

The funnel 4 is an extension of the seat cover 2, which helps funnel the specimen into the collection bag 5. It is attached to the inside of collection bag 5. It may be made from the same material as the seat cover and be of sufficient strength to hold the collection bag above the water line when full. The collection bag connects to the funnel from the opening on the top edge of the bag. The bag hangs horizontally so as not to reach water level (Average water line is 6"-7"). The collection bag "in-situ" may be approximately 5"-6" wide and 4"-5" tall. The collection bag may be constructed out of non-latex, PVC type or similar material similar to IV bags. The plastic should also be sufficiently smooth and/or have a surface conducive to channeling the specimen into the collection bag as smoothly, cleanly and expeditiously as possible. This could include a silicone-type coating. The seat cover/funnel should be made of a material that is flushable if environmentally feasible and appropriate. The opening of the collection bag is large enough to accommodate the funnel 4 and sample collection: approximately 3" wide. After use it can be easily sealed by both a primary and secondary seal system as will be explained below. As an alternate a combination of the primary seal tab 7 and tear line pull handle 9 might be integrated into one handle to perform both "functions" at the same time. Thereby, separating the funnel from the collection bag and exposing the primary seal with one pull from a single handle.

The proposed stool containment, collection, and specimen disbursement system has multiple layers of sealing capability to facilitate easier collection, protect sample from bio-contamination and provide easier functionality for patients, diagnostic centers and labs. It includes a variety of features that enable distributing, re-sealing and extracting specific sample quantities when and as needed.

A perforated tear line 8 serves as the primary connection between the funnel 4 and the collection bag 5. This perforated tear line connects funnel 4 to both inside walls of the collection bag. The tear lines can be also seen in FIG. 2. The perforations should be sufficiently strong to remain intact and keep the collection bag elevated above the water line during and after sample collection; approximately 1.25 lbs max weight. The collection bag connects to the funnel from the opening on the top edge of the bag. The bag hangs horizontally so as not to reach water level (Average water line is 6"-7"). The collection bag is constructed out of non-latex, PVC material similar to IV bags. The collection bag has a re-sealable, variable flow rate nozzle 11 on one side of the bag. The collection bag "in-situ" should be approximately 5"-6" wide and 4"-5" tall. After sample collection, the funnel is separated from the collection bag via a pull handle 9, aided by the perforations on the tear line. The pull handle 9 connected to one side of the tear line 8 of sufficient strength to separate the funnel from the collection bag 5.

A primary adhesive seal with peel off backing seals the opening of the collection bag 5 after sample collection and funnel removal via tear line handle 9. It is secured by the patient to create a primary seal at the top opening of the collection bag in order to prevent leaking or spillage. The primary adhesive seal is exposed via primary seal tab 7 and sealed after the funnel 4 has been detached from the collection bag. The adhesive backing should be easily reachable and removable from outside the bag opening using a pull-tab. This tab 7 connects to one side of the adhesive backing 6. The seal should be up to 4" inches wide by 1" inch tall which should be sufficient to securely close the entire opening 14 of the collection bag after funnel removal. The seal is about ½" longer than the opening on both sides for better adhesion and spill prevention.

The primary seal tab 7 is a small tab of sufficient size and strength to remove the primary seal backing 6 from the adhesive strip on the primary seal. The tab should be easily reachable from outside the funnel 4 and collection bag opening 14.

A perforated tear line 8 serves as the primary connection between the funnel 4 and the collection bag 5. Perforated tear line 8 should connect the funnel to both inside walls of the collection bag. The perforations should be sufficiently strong to remain intact and keep the collection bag elevated above the water line during and after sample collection; approximately 1.25 lbs max weight. After sample collection, the funnel is separated from the collection bag via a pull handle 9, aided by the perforations on the tear line. The pull handle 9 connected to one side of the tear line 8 of sufficient strength to separate the funnel from the collection bag 5.

The opening 14 of collection bag 5 is large enough to accommodate the funnel 4 and sample collection. It is sealed by both primary 6 and secondary 10 adhesive seals.

Figure 2:
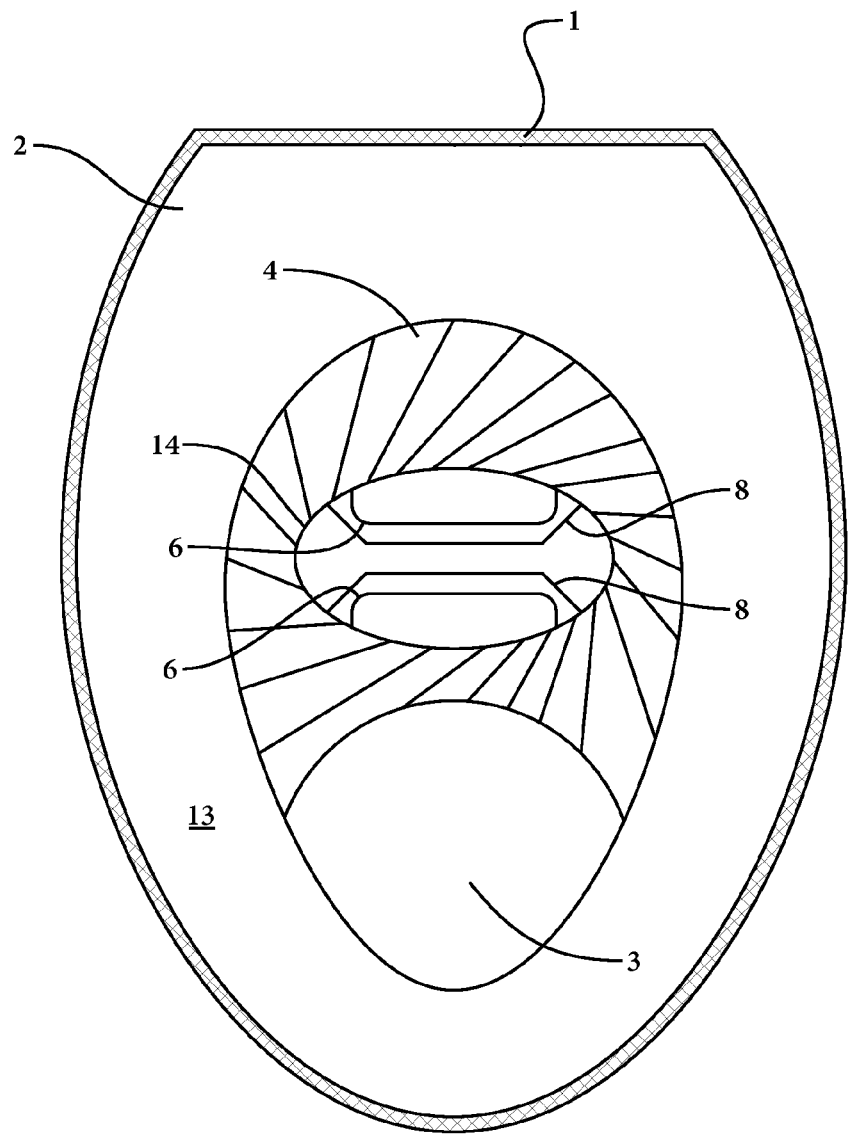
FIG. 2 is an overhead view of the device on toilet prior to use.

A funnel urine opening 3, shown in FIG. 2 has an opening large enough to enable urine to directly flow into the toilet bowl during the specimen collection process and avoid contamination of the stool specimen. The opening will be sufficiently large to accommodate both male and female anatomy.

In use and after sample collection, the patient/user can then lift the complete system from the toilet. The funnel is then separated from the collection bag via a pull handle 9. The patient/user can grab pull handle and pull upward with enough force to then separate the entire funnel, including elastic band 1 and seat cover 2. A clean separation is aided by the perforations on the tear line.

Once the polymeric funnel, elastic band, and polymeric seat cover have been removed closing seal 6 can then quickly complete the primary seal. This is done by the patient pulling on primary pull seal tab 7, which strips off the adhesive seal cover sheet, exposing the adhesive layer of the primary seal, and covers the opening into the collection bag to provide the primary seal. The primary seal with adhesive then seals the opening of the collection bag and is secured by the patient to create a primary seal that prevents leaks or spillage. The primary adhesive seal is exposed and sealed after the funnel has been detached from the collection bag. The adhesive backing is easily reachable and removable from outside the bag opening after the funnel has been removed. This could be a looped or flat tab that connects to seal 6 to enable the adhesive backing to be removed. The seal should be up to 3 inches wide by 1 inch tall which should be sufficient to securely close the entire opening of the collection bag after funnel removal.

Referring back to FIG. 1, the dotted line 10 designates a larger secondary adhesive seal and label flap that in this side view lies along the outside of collection bag 5 and is therefore not visible in this drawing. That secondary adhesive seal and label flap also has a peel off backing that when removed exposes the adhesive so that the larger secondary adhesive seal and label flap can be draped over the top of the collection bag to ensure an airtight seal and bio-containment.

The collection bag 5 may accommodate a label that includes patient information and a list of requested tests and assays. This label area could be on the larger secondary adhesive seal and label flap 10. A custom label can be supplied using a pre-populated label template. The label could have check boxes next to each requested test in order to verify completion.

FIG. 1 also shows is a re-sealable, variable flow rate nozzle 11 on one side of collection bag 5. The nozzle is re-sealable using a snap cap 13 and twist-to-open valve with ridges for sure grip. The twist valve also provides variable flow-rate for specimen distribution. The valve can be twisted to close completely and re-capped for storage or use at another time.

The valve extends into collection bag 5 approximately two inches via a plastic spindle that connects directly to a round edged (non-perforating) fanned tip 12. As the nozzle is twisted to open and adjust the flow rate, the inside fanned-tip rotates accordingly. This enables higher flow rates for more dense or hardened samples.

Figure 3:
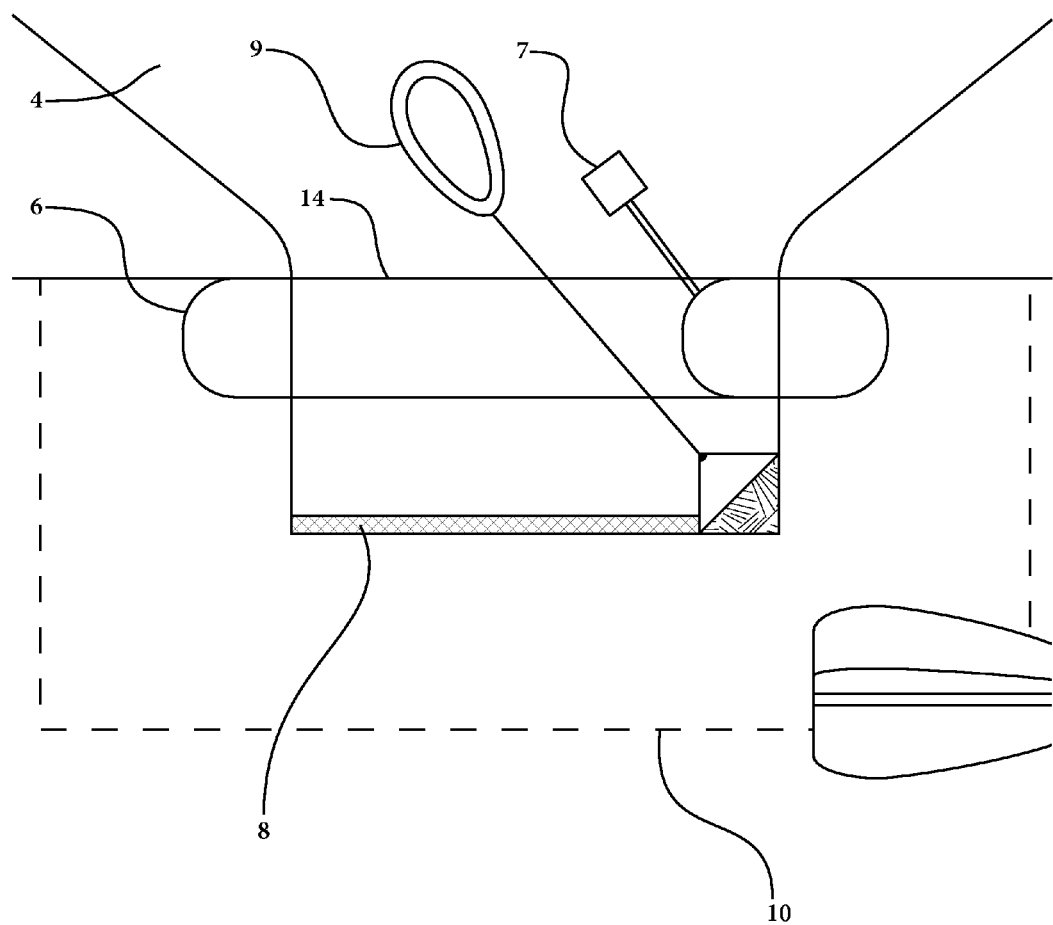
FIG. 3 is a close-up/exploded view of primary seal with adhesive strip being exposed via pull-tab.

FIG. 3 Is a close-up/exploded view of primary seal with adhesive strip being exposed via pull-tab 7. As pull-tab 7 is pulled the perforated funnel is detached along the tear line 8 from the collection bag via pull-handle. Once the funnel, elastic band, and seat cover have been removed closing the primary seal 6 can then quickly do the first level of sealing and containment. This is done by the patient (or lab technician) pulling on primary pull seal tab 7, which strips off the adhesive seal cover sheet, exposing the adhesive layer of the primary seal 6, and covers the opening into the collection bag to provide the primary seal. The primary seal 6 with adhesive then seals the opening of the collection bag and is secured by the patient to create a primary seal and prevent spillage.

After the primary seal is in place the secondary seal 10 (with its own adhesive) is then draped over the primary seal to ensure an airtight seal and bio-containment.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

The invention claimed is:

1. A stool collection, containment, and specimen disbursement system comprising:
   a. a polymeric toilet seat cover that can fit over a variety of toilet seats;
   b. an elastic band that is configured to secure the toilet seat cover to the variety of toilet seats;
   c. a polymeric funnel that extends from the toilet seat cover into a toilet bowl and is connected to the inside of a polymeric collection bag by perforated tear lines on either side of the collection bag;
   d. an opening in the polymeric funnel large enough to allow urine to bypass the collection bag and flow directly into the toilet bowl;
   e. a looped handle connected to the perforated tear lines and used to tear the funnel away from the collection bag;
   f. a primary seal with adhesive at the opening of the containment bag with an attached primary pull seal tab that allows the removal of an adhesive cover sheet; and
   g. a larger secondary seal with adhesive positioned outside of the funnel along the outside of the collection bag with a removable adhesive cover sheet.

2. The stool collection, containment, and specimen disbursement system of claim 1 further comprising a re-sealable nozzle on one side of the collection bag for specimen distribution.

3. The stool collection, containment, and specimen disbursement system of claim 1 wherein the polymeric collection bag is a non-latex material.

4. The stool collection, containment, and specimen disbursement system of claim 1 further comprising a label affixed to the larger secondary seal that includes patient and required test information.

5. A method for stool collection, containment, and specimen disbursement by a patient using the system of claim 1 comprising:
   a. placing the stool collection, containment, and specimen disbursement system into a toilet by fitting the polymeric seat cover over a toilet seat of the toilet;
   b. using the placed stool collection, containment, and specimen disbursement system to collect a specimen;
   c. lifting the complete stool collection, containment, and specimen disbursement system from the toilet;
   d. pulling upward on the looped handle connected to the perforated tear lines to separate the polymeric funnel, including the elastic band and the polymeric seat cover from the polymeric collection bag;
   e. pulling upward on the primary pull seal tab, exposing the adhesive of the primary seal;
   f. securing the primary seal over the opening of the containment bag; and
   g. removing the removable adhesive cover sheet of the larger secondary seal positioned outside of the funnel and drape the larger secondary seal over the top of the collection bag to create an airtight seal and bio-containment.

6. The method for stool collection, containment, and specimen disbursement by a patient using the method of claim 5 further comprising entering patient and required test information onto a label affixed to the larger secondary seal draped over the top of the collection bag.

7. The method for stool collection, containment, and specimen disbursement by a patient using the method of claim 5 further comprising utilizing a re-sealable nozzle on the side of the collection bag for specimen distribution.

8. The stool collection, containment, and specimen disbursement system of claim 2 wherein the re-sealable nozzle is a variable flow rate nozzle.

9. The method for stool collection, containment, and specimen disbursement by a patient using the method of claim 7 wherein the re-sealable nozzle is a variable flow rate nozzle.

* * * * *